United States Patent
Amory et al.

(10) Patent No.: US 6,190,904 B1
(45) Date of Patent: Feb. 20, 2001

(54) HIGH-ALKALINE PROTEASE AND ITS USE ARGININE-SUBSTITUTED SUBTILISIN COMPOSITION AND USE

(75) Inventors: Antoine Amory, Rixensart; André Clippe, Brussels, both of (BE); Gerhard Konieczny-Janda, Pattensen (DE); Hubert Herrmann, Nienburg (DE); Karsten Börner, Sehnde (DE)

(73) Assignee: Genecor International, Inc., Rochester, NY (US)

( * ) Notice: Under 35 U.S.C. 154(b), the term of this patent shall be extended for 0 days.

(21) Appl. No.: 08/716,293

(22) PCT Filed: Mar. 27, 1995

(86) PCT No.: PCT/EP95/01141

§ 371 Date: Dec. 18, 1996

§ 102(e) Date: Dec. 18, 1996

(87) PCT Pub. No.: WO95/27049

PCT Pub. Date: Oct. 12, 1995

(30) Foreign Application Priority Data

Mar. 31, 1994 (DE) .................................................. 44 11 223

(51) Int. Cl.[7] .............................. C12N 9/54; C11D 3/386; C14C 1/00; C14C 1/06

(52) U.S. Cl. .................. 435/264; 435/69.1; 435/221; 435/265; 435/471; 536/23.2; 510/392

(58) Field of Search ........................................... 435/220, 221, 435/222, 69.1, 265, 264; 510/276, 218, 300, 320, 392; 8/94.19 R, 401

(56) References Cited

U.S. PATENT DOCUMENTS

| 4,594,362 | * | 6/1986 | Smith et al. | 521/52 |
| 4,980,288 | * | 12/1990 | Bryan et al. | 435/222 |
| 5,116,741 | * | 5/1992 | Bryan et al. | 435/87 |
| 5,352,603 | * | 10/1994 | Vetter et al. | 435/221 |
| 5,397,705 | * | 3/1995 | Zukowski et al. | 435/222 |
| 5,665,587 | * | 9/1997 | Aaslyng et al. | 435/221 |
| 5,880,080 | | 3/1999 | Amory et al. | 510/320 |

FOREIGN PATENT DOCUMENTS

| 1800508 | * | 5/1969 | (DE) . |
| 503 346 | * | 9/1902 | (EP) . |
| 328 229 | * | 8/1989 | (EP) . |
| 405 901 | * | 1/1991 | (EP) . |
| 415 296 | * | 3/1991 | (EP) . |
| 91/02972 | * | 3/1991 | (WO) . |
| WO 95/30011 | * | 3/1995 | (WO) . |
| 95/27049 | * | 10/1995 | (WO) . |

OTHER PUBLICATIONS

Siezen, R. J., et al., Protein Engineering, vol. 4, "Homology modelling and protein engineering strategy of subtilases, the family of subtilisin–like serine proteases", pp. 719–737, 1991.*

* cited by examiner

Primary Examiner—Ponnathapu Achutamurthy
Assistant Examiner—William W. Moore (57) ABSTRACT

The invention relates to a novel high-alkaline protease, its use in the industrial or domestic fields and also compositions for said uses containing this protease. The protease of the invention is a selected triple mutant derived from certain precursor proteases from the subtilisin group, especially of the "subtilisin 309" type.

12 Claims, 5 Drawing Sheets

SEQUENCE PROTOCOL

INFORMATION RELATING TO SEQ ID NO: 1:

SEQUENCE CHARACTERISTICS:
        LENGTH: 380 amino acids
        TYPE: amino acid
        TOPOLOGY: linear     TYPE OF MOLECULE: Protein     ORIGIN:
        ORGANISM: *Bacillus alcalophilus*
        STRAIN: HA1, DSM 5466

PROPERTIES:
        NAME/KEY: mature peptide
        POSITION: 1 .. 269

SEQUENCE DESCRIPTION: SEQ ID NO: 1:

```
Met Lys Lys Pro Leu Gly Lys Ile Val Ala Ser Thr Ala Leu Leu
   -110            -105             -100

Ile Ser Val Ala Phe Ser Ser Ser Ile Ala Ser Ala Ala Glu Glu
    -95              -90              -85

Ala Lys Glu Lys Tyr Leu Ile Gly Phe Asn Glu Gln Glu Ala Val
    -80              -75              -70

Ser Glu Phe Val Glu Gln Val Glu Ala Asn Asp Glu Val Ala Ile
    -65              -60              -55

Leu Ser Glu Glu Glu Glu Val Glu Ile Glu Leu Leu His Glu Phe
    -50              -45              -40

Glu Thr Ile Pro Val Leu Ser Val Glu Leu Ser Pro Glu Asp Val
    -35              -30              -25

Asp Ala Leu Glu Leu Asp Pro Ala Ile Ser Tyr Ile Glu Glu Asp
    -20              -15              -10

Ala Glu Val Thr Thr Met Ala Gln Ser Val Pro Trp Gly Ile Ser
     -5               1                5

Arg Val Gln Ala Pro Ala Ala His Asn Arg Gly Leu Thr Gly Ser
     10               15               20

Gly Val Lys Val Ala Val Leu Asp Thr Gly Ile Ser Thr His Pro
     25               30               35
```

FIG._1A

```
Asp Leu Asn Ile Arg Gly Gly Ala Ser Phe Val Pro Gly Glu Pro
40              45                  50
Ser Thr Gln Asp Gly Asn Gly His Gly Thr His Val Ala Gly Thr
55              60                  65
Ile Ala Ala Leu Asn Asn Ser Ile Gly Val Leu Gly Val Ala Pro
70              75                  80
Ser Ala Glu Leu Tyr Ala Val Lys Val Leu Gly Ala Ser Gly Ser
85              90                  95
Gly Ser Val Ser Ser Ile Ala Gln Gly Leu Glu Trp Ala Gly Asn
100             105                 110
Asn Gly Met His Val Ala Asn Leu Ser Leu Gly Ser Pro Ser Pro
115             120                 125
Ser Ala Thr Leu Glu Gln Ala Val Asn Ser Ala Thr Ser Arg Gly
130             135                 140
Val Leu Val Val Ala Ala Ser Gly Asn Ser Gly Ala Gly Ser Ile
145             150                 155
Ser Tyr Pro Ala Arg Tyr Ala Asn Ala Met Ala Val Gly Ala Thr
160             165                 170
Asp Gln Asn Asn Asn Arg Ala Ser Phe Ser Gln Tyr Gly Ala Gly
175             180                 185
Leu Asp Ile Val Ala Pro Gly Val Asn Val Gln Ser Thr Tyr Pro
190             195                 200
Gly Ser Thr Tyr Ala Ser Leu Asn Gly Thr Ser Met Ala Thr Pro
205             210                 215
His Val Ala Gly Ala Ala Ala Leu Val Lys Gln Lys Asn Pro Ser
220             225                 230
Trp Ser Asn Val Gln Ile Arg Asn His Leu Lys Asn Thr Ala Thr
235             240                 245
Ser Leu Gly Ser Thr Asn Leu Tyr Gly Ser Gly Leu Val Asn Ala
250             255                 260
Glu Ala Ala Thr Arg
265             269
```

HIGH-ALKALINE PROTEASE AND ITS USE ARGININE-SUBSTITUTED SUBTILISIN COMPOSITION AND USE

This application is the U.S. national stage application of PCT/EP 95/01141, filed Mar. 27, 1995, which claims priority to German patent application number P44 11 223.8, filed Mar. 31, 1994.

The subject matter of this invention concerns a new high-alkaline protease, its use in the industrial and domestic field, and compositions for the applications mentioned which contain this protease.

The use of protease-containing compositions in industrial applications or processes is well known. For example, in commercial laundry establishments, proteases have long been used, for example, to clean blood-stained hospital linen as well as protective clothes worn in meat-processing plants. For the production of leather, it is still normal practice in the leather treatment industry, for example, to remove the hair from skins and hides in an alkaline processing stage in the so-called beamhouse, which creates the prerequisites for hair removal and which causes the necessary skin digestion, often still using questionable and unsafe chemicals (e.g., inorganic sulfides). Although recently enzymatically supported liming processes (hair removal processes) have been proposed—especially using tryptic enzymes or fungal or bacterial proteases and sometimes even carbohydrolases—in practice, these enzymatic processes for the removal of hair from hides and skins have been applied almost exclusively to hides and skins of small animals and even in this area, the use has been rather restricted. For the removal of hair of large animals, on the other hand, the enzymatic hair removal process has so far not gained any acceptance at all, mainly because in many cases, hair removal is incomplete and because the collagen grain membrane is damaged or because too much of the skin substance is destroyed. In addition, the use of a certain percentage of alkaline proteases during liming with a reduced quantity of chemicals (e.g., sulfides) has been investigated. Although the use of enzymes makes it possible to markedly reduce the quantity of chemicals (e.g., sulfide) and although excellent surface yields with little cicatricial contraction are obtained, leather produced in this manner tends toward grain pipeyness, toward a loose flame scarring structure, and toward a coarse appearance which sometimes resembles the grain of nubuck leather. To the extent that proteases are presently used in the leather manufacturing industry (main soaking cycle and liming), these prior-art proteases, while having high pH values (pH=11 to 13), are not sufficiently effective and have a relatively low activity at the treatment temperatures (28° C. to 30° C.) normally encountered in the limeyard.

Due to the fact that the conditions in industrial processes are more drastic than those in domestic applications (e.g., as a household detergent), the proteases used must meet especially stringent requirements with respect to stability, acceptance of the prevailing environment, and performance. In addition to a satisfactory stability and activity at high alkaline pH values, the proteases should, on the one hand, have an excellent temperature resistance so as to yield good results at a low concentration over the longest possible time at a temperature that for a given industrial application can be very high and, on the other hand, they should be sufficiently active in certain applications (e.g., leather manufacture) even at relatively low temperatures (approximately 30° C.). Furthermore, the alkaline proteases used should be as resistant as possible to the chemicals and ingredients that are conventionally used in industrial processes (e.g., surfactants, bleaching agents, or disinfecting agents, chemicals, and other constituents).

Thus, the need for other alkaline proteases that are suitable for industrial applications, e.g., proteases for industrial textile laundering processes, industrial surface cleaning, or leather treatments and leather manufacture, is undiminished.

Therefore, the problem to be solved by this invention was to create a new alkaline protease which is suitable especially for use in industrial processes and which, in addition, can also be used to advantage for domestic applications.

It was discovered that the alkaline bacillus protease described below can be used highly effectively in a number of industrial processes. Thus, one of the subject matters of this invention concerns an alkaline protease and its use especially in compositions for industrial applications as well as in the domestic field, such as proposed in the claims and described in greater detail below.

Figure 1A:
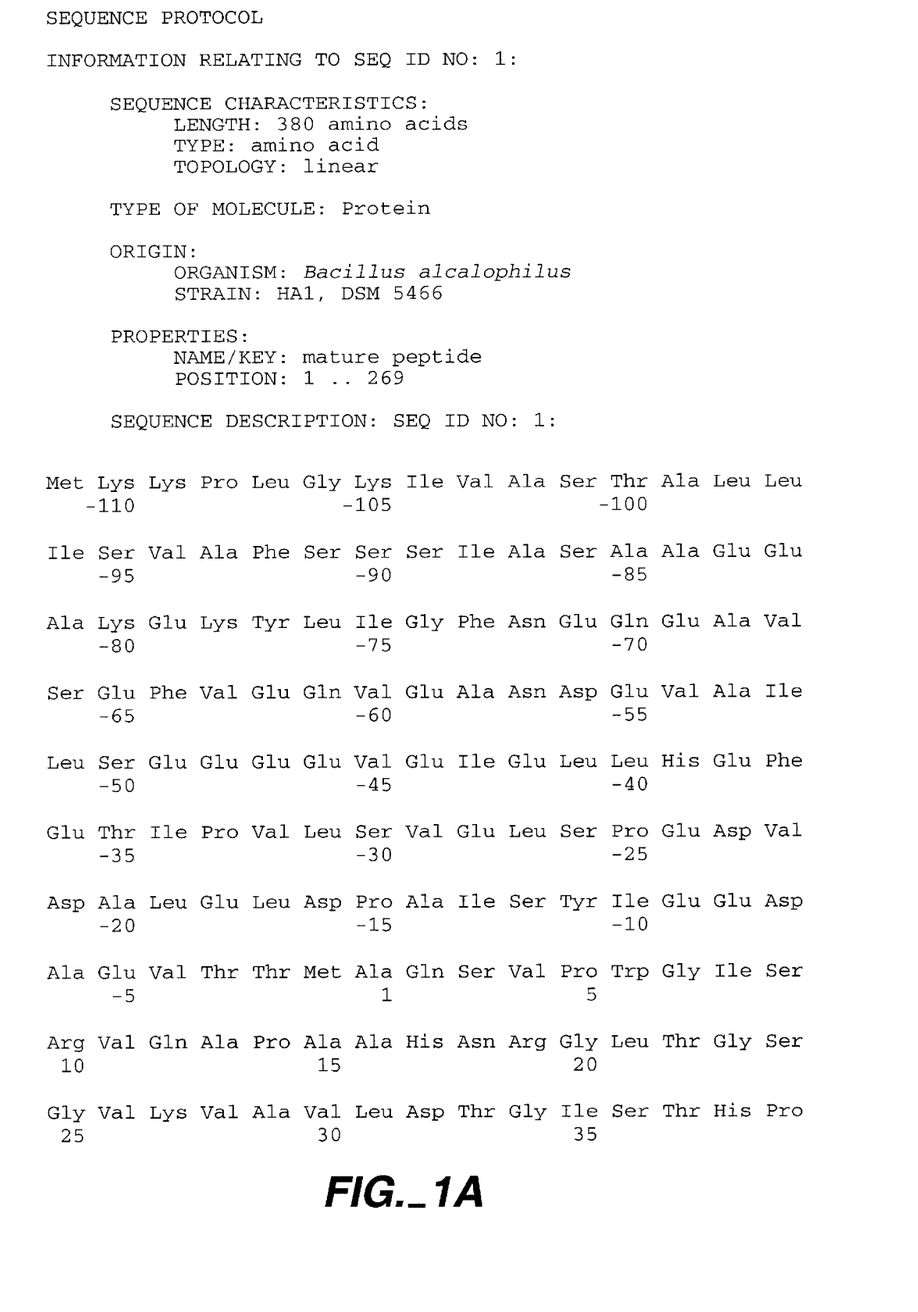
Figure 1B:
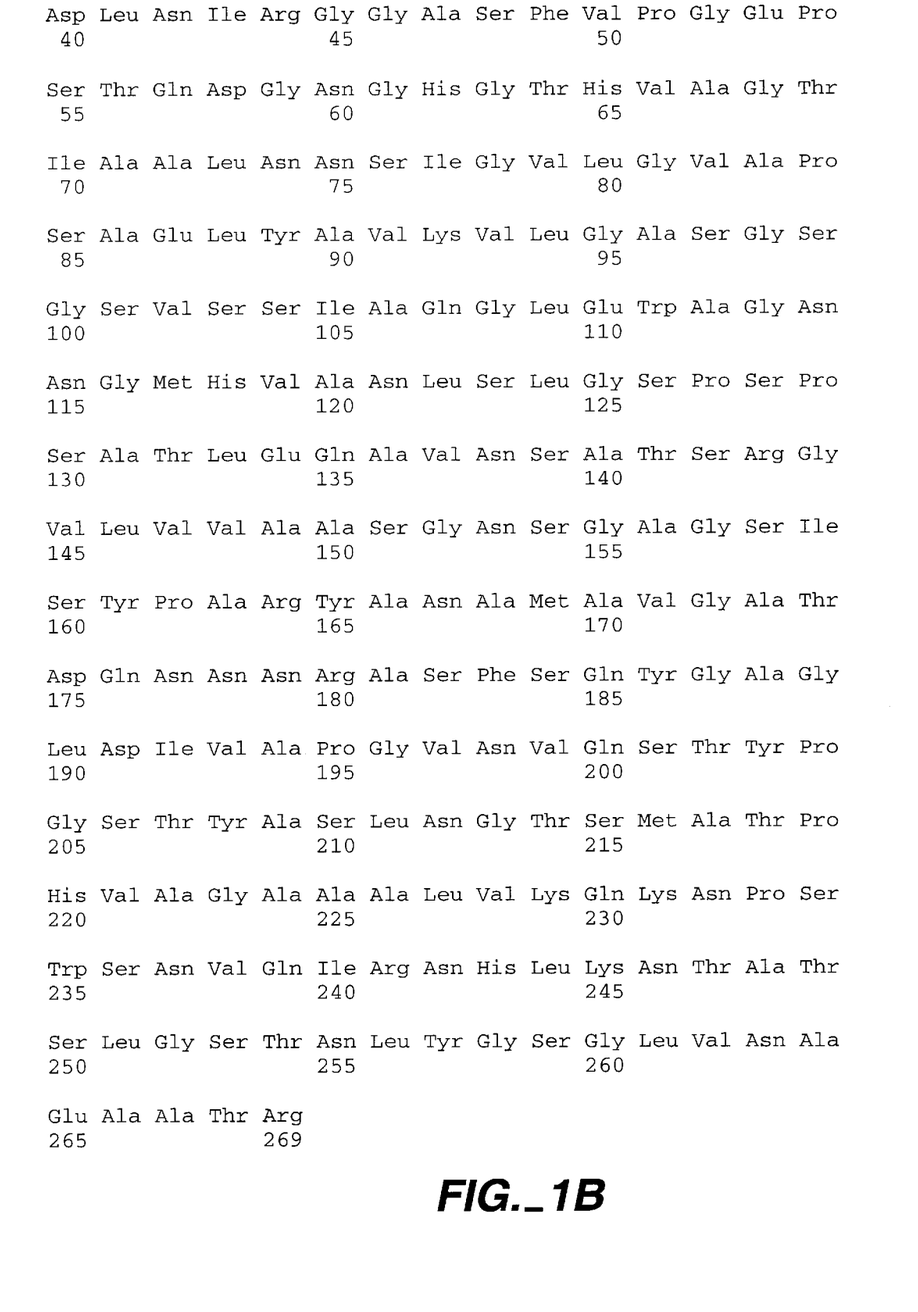

Therefore, the subject matter of this invention concerns a high-alkaline protease which is characterized by the fact that it contains an underlying amino acid sequence with a minimum of a 95%, preferably with a minimum of a 98%, homology with respect to the amino acid sequence shown in FIG. 1 and that it is distinguished from this sequence by a triple mutation in the positions 42/114/115 of FIG. 1 or that is distinguished in the three positions homologous thereto by the fact that arginine has been substituted for the amino acids in the relevant positions.

The alkaline bacillus protease mentioned has a molecular weight of approximately 26,000 to 28,000 g/mol, measured by means of SDS polyacrylamide gel electrophoresis against references proteins with a known molecular weight. The optimum pH value which was determined with soluble model substrates in an analytical test is approximately pH 10.5, with the optimum pH value being defined as that pH range in which the protease has a maximum proteolytic activity. The pH activity is higher than in the original protease (according to FIG. 1); the optimum effect extends further into the more alkaline range and is pH 10.5 to 11.5. In addition, the mentioned alkaline bacillus protease according to this invention has an excellent pH stability and temperature resistance. Thus, this protease is an extremely high-alkaline protease which is effective in a pH range so far not reached by prior-art proteases.

In this context, homology with respect to the amino acid sequence shown in FIG. 1 is defined as the structural relationship between the relevant amino acid sequences and the amino acid sequence shown in FIG. 1. To determine the homology, the segments of the amino acid sequence of FIG. 1 which structurally correspond to one another and of the amino acid sequence with which they are to be compared are made to coincide in such a way that a maximum structural agreement between the amino acid sequences exists, and differences caused by the deletion or insertion of individual amino acids are taken into consideration and are compensated for by appropriate rearrangements of sequence segments. The number of amino acids which now match one another in the sequences ("homologous positions"), relative to the total number of the amino acids that are contained in the sequence of FIG. 1, is the homology in %. Differences in the sequences can be caused by variation and insertion and by deletion of amino acids. It is therefore obvious that, if alkaline proteases are used which are at least 95% homologous with respect to FIG. 1, the amino acid positions named with respect to FIG. 1 refer to the positions of the protease used which are homologous thereto. Deletions or insertions in the amino acid sequences of the proteases that are homologous with respect to FIG. 1 can lead to a relative rearrangement of the amino acid positions so that the numerical notations of the amino acid positions that correspond to one another need not be identical in homologous fragments of amino acid sequences that are homologous with respect to one another, i.e., it is possible for slight numerical rearrangements to develop relative to the individual numbering of the amino acid positions.

In a preferred modification of this invention, the high-alkaline protease is characterized by an underlying amino acid sequence which is substantially identical to the amino acid sequence shown in FIG. 1 and which differs from this amino acid sequence by a triple mutation in positions 42/114/115 of FIG. 1 in that the amino acids in the relevant positions have been replaced by arginine. The term "substantially identical" amino acid sequence is here defined to indicate that, with the exception of the mentioned triple mutation N42R/N114R/N115R, only a few other, i.e., especially only up to 6 (corresponding to an approximately 98% homology or more), amino acids can differ from the amino acids shown in the sequence of FIG. 1. The amino acid sequence underlying the high-alkaline protease according to this invention thus corresponds substantially to those proteases which can be designated as being of the "subtilisin 309"-type since the amino acid sequence of the "subtilisin 309" known from prior art is identical to the amino acid sequence shown in FIG. 1. A protease which is nearly identical thereto and which, with the exception of position 85, coincides with the amino acid sequence in FIG. 1, has been described in prior art as a protease from Bacillus nov. species PB92 (see European Patent Application EP 283, 075). The protease from Bacillus PB92 differs only insignificantly from the amino acid sequence shown in FIG. 1 in that in position 85, the natural difference asparagine instead of serine is present, and it is therefore considered to be "subtilisin 309"-type protease. Another protease which is substantially identical to "subtilisin 309" and which, with the exception of the five positions 97, 99, 101, 102, and 157, coincides with the amino acid sequence in FIG. 1, has been described in prior art as protease from *Bacillus lentus* (see International Patent Publication WO 91/02792 and U.S. Pat. No. 5,352,604) ("BLAP"). Protease "BLAP" from *Bacillus lentus* differs only insignificantly from the amino acid sequence shown in FIG. 1 in that natural differences exist in five positions: 97D, 99R, 101A, 102I, and 157S. A variant of "BLAP" differs additionally due to a sixth natural difference threonine instead of serine in position 3 (alkaline protease which has also been described in International Patent Publication WO 91/02792 and U.S. Pat. No. 5,352,604). D=Asp=asparagic acid, R=Arg=arginine, A=Ala=alanine, I=Ile=isoleucine, S=Ser=serine, T=Thr=threonine. "BLAP" and its variant with the mutation S3T thus have an approximately 98% homology with respect to the amino acid sequence of FIG. 1 and are accordingly considered to be "subtilisin 309"-type proteases. Therefore, this invention preferably concerns high-alkaline proteases with the triple mutation N42R / N114R / N115R, the underlying amino acid sequence of which is identical to the amino acid sequence shown in FIG. 1 or differs therefrom only in position 85 due to the natural difference asparagine instead of serine or only in the following five position due to the natural differences 97D/99R/101A/102I/157S or only in the six positions because of the natural differences 3T/97D/99R/101A/102I/157S.

The alkaline bacillus protease underlying the proteases according to this invention can be obtained from the bacillus strain (with the amino acid sequence of FIG. 1) that was deposited under No. 5466 with the DSM [Deutsche Sammlung von Mikroorganismen und Zellkulturen, German Collection of Microorganisms and Cell Cultures, the German equivalent of the ATCC] on Jul. 28, 1989; further details, especially the isolation, concerning this strain have been described in the European Patent Application EP 415,296. The variant, which differs in position 85, of the protease underlying the protease mutants according to this invention can be similarly obtained by cultivating the Bacillus nov. species PB92 (as described in the European Patent Application EP 283,075 and in the corresponding U.S. Pat. No. 5,217,878). The variants, which differ in positions 97/99/101/102/157 or in positions 3/97/99/101/102/157, of the protease underlying the protease mutants according to this invention can be similarly obtained by cultivating *Bacillus lentus* or, after appropriate transformation, even in *Bacillus licheniformis* (as described in the International Patent Publication WO 91/02792 and in the corresponding U.S. Pat. No. 5,352,604). The variants in position 85 and the variants "BLAP" can be produced by means of producing corresponding point mutations in the positions mentioned from the protease with the amino acid sequence shown in FIG. 1. From the above-mentioned proteases of the "subtilisin 309"-type underlying the protease mutants according to this invention, it is possible to produce the high-alkaline proteases according to this invention with the triple mutation N42R/N114R/N115R according to substantially known methods by means of combined or consecutive point mutations in the amino acid sequence of the precursor protease of the "subtilisin 309"-type. The European Patent Application EP 415,296 describes how such point mutations processes relative to individual amino acid positions are carried out, and the procedure described in this application can be used to produce the triple mutations for the production of the proteases according to this invention. With reference to the patent applications mentioned above, the contents of the prior patent applications relating to this subject, especially of the European Patent Application EP 415,296 (and the corresponding U.S. Pat. No. 5,352,603), is therefore expressly incorporated into this application.

In a highly preferred modification of this invention, the high-alkaline protease according to this invention with the triple mutation N42R/N114R/N115R is derived from an underlying alkaline bacillus protease from strain DSM 5466 with an underlying amino acid sequence that is identical to that shown in FIG. 1. In the mutations which are given in the shorthand notational convention, the numbers refer to the position in the amino acid sequence (see FIG. 1). The original amino acid precedes the number and the new amino acid which was introduced by mutation into the amino acid sequence in the relevant position follows the number. To identify the amino acids, the one-letter code is used: N stands for asparagine (Asp) and R stands for arginine (Arg). As already mentioned above, the amino acid exchanges can be obtained according to substantially known methods by point mutation in the amino acid sequence, which procedure has been described, for example, in the European Patent Application EP 415,296.

The high-alkaline bacillus protease mutants N42R/N114R/N115R according to this invention are exceptionally active under conditions which generally prevail in industrial applications—high pH values, high temperatures, short application times. The protease mutants according to this invention are also surprisingly resistant to the constituents contained in the formulation that are conventionally used in industrial processes, e.g., in industrial textile laundering processes. The high-alkaline bacillus protease mutants according to this invention can therefore be used to considerable advantage in industrial processes, such as in industrial textile laundering processes, in any type of industrial surface cleaning process, in leather treatment processes, especially, for example, in the manufacture of leather. An industrial application of the protease according to this invention in industrial textile laundering establishments has been described in greater detail, for example, in the German Patent Application DE 4,411,223; thus, the high-alkaline bacillus protease mutant according to this invention can be used, for example, in industrial large drum washing machines or in fully continuous or countercurrent washing plants. It is especially preferred if in the so-called multiliquor processes, e.g., in the two-bath process consisting of a preliminary washing and a clear rinsing cycle, the alkaline bacillus protease according to this invention is added to the preliminary washing cycle. Using substantially known methods, preliminary washing can be carried out under the conditions generally used in industrial textile laundering processes, e.g., at temperatures from 30° C. to 70° C., with detergent ingredients that are normally used in this washing cycle. In the case of contaminations with a high protein content, for example, blood-stained laundry from hospitals or, e.g., laundry from institutional kitchens or meat-processing plants, the proteases mentioned can also be successfully used, for example, in a rinsing cycle, which precedes the preliminary washing cycle, with clear cold or recycled warm water and otherwise conventionally added detergent ingredients. In addition, the alkaline bacillus protease mutants according to this invention can also be used to advantage in other industrial textile laundering processes, e.g., in industrial laundering processes which specifically target special types of textiles and contaminations, for example, to disinfect fabrics that have been used in hospitals. Details can be found in the German Patent Application DE 4,411,223.

Another application area in which this invention can be successfully used is the cleaning of (hard) surfaces in industrial plants, preferably in slaughtering plants of the food industry, in institutional kitchens in grill restaurants, etc.

All surfaces which during the production or processing of food come into contact with this food have to be cleaned at regular intervals. Different branches (e.g., the beverage, canning, and sugar industry and the milk-, meat-, and fat-processing industry) have to deal with different types of contaminations. To remove these contaminations, prior art provides for a relatively large range of different cleaning agents. First, these cleaning agents have to remove protein, fat, and carbohydrate stains. In addition to organic contaminations, there are inorganic contaminations that must be removed. Therefore, the cleaning agents consist of a mixture of different ingredients which serve specific functions during the cleaning process. These cleaning agents are commercially available in the form of powders or liquids, in rarer cases also in the form of pastes, and, with a few exceptions, have to be diluted by the consumer with water to concentrations of 0.5 to 2 wt %. The enzymes used in the special surface cleaning agents are especially proteases and amylases for removing protein- and starch-containing stains. The use of the protease triple mutant according to this invention in such cleaning agents for cleaning hard surfaces is recommended especially in cases in which the susceptibility to corrosion of the contaminated material (especially in the case of light metals, such as aluminum and its alloys) makes the use of stronger acid or alkaline products impossible, for example, for cleaning membranes in hyperfiltration plants (reverse osmosis).

Conventional ingredients of this type of special cleaning agents for cleaning hard surfaces in the food industry include (in addition to the enzymes already mentioned earlier) especially components which break down dirt and which, as the main ingredient in such cleaning agents, serve to dissolve the dirt, mostly alkaline reacting (e.g. sodium or potassium hydroxide, sodium or potassium carbonate) alkaline salts of orthophosphoric acid or of other organic acids, and different types of soda and potash water glass with different silicon dioxide/sodium oxide ratios ($SiO_2:Na_2O=$ 0.7–3.3); other ingredients to be mentioned include surface-active substances, especially for the removal of fatty dirt (anionic surfactants, e.g., fatty alcohol sulfates, alkyl benzene sulfonates and soaps; also, nonionic fatty alcohol ethers and alkyl phenol glycol ethers); corrosion-protection agents, especially for use on light metals, such as aluminum and its alloys, to avoid corrosive wear, e.g., in the alkaline range, sodium silicate, and in the acid range, a number of inhibitors that are specifically effective on acid and material; antifroth agents, e.g., paraffin oil and silicones, preferably special ethoxylation and propoxylation products.

Below, two cleaning agent compositions, in which the protease triple mutant according to this invention is used, for cleaning hard surfaces in two special fields of applications are listed:

Cleaning agent for cleaning grills:
1.0 wt % of Walocel HT 30000 PFV
0.5 wt % of Sequinon 40 Na 32
25 wt % of potassium hydroxide solution (50 wt %)
4 wt % of Rewoteric AM VSF
3 wt % of protease triple mutant (activity 300,000 DU[Delft units]/mL±5%)
66.5 wt % of water High-pressure active cleaning agent:
5 wt % of fatty alcohol ether sulfate (28 wt %)
10 wt % of Sequinon 40 Na 32
10 wt % of sodium hydroxide solution (40 wt %)
2 wt % of sodium cumene sulfate (40 wt %)
3 wt % of protease triple mutant (activity 300,000 DU/mL±5%)
70 wt % of water Another application area in which the high-alkaline protease mutants according to this invention can be used to advantage is the field of leather treatment, especially the leather manufacturing industry. In this field of application, the protease mutant according to this invention is used especially in processes for hair removal skins and hides, and in particular in the main soaking cycle and/or in liming.

The protease mutants according to this invention are excellent for use in the manufacture of leather. The manufacture of leather comprises, among other things, the following steps:

a) First soaking stage for removing salt, dirt and dung
b) Main soaking stage for swelling the skin and dissolving water-soluble proteins
c) Liming for hair removal, for the principal digestion and for the second swelling (pelting); "pelt" is defined as the hairless digested skin produced in this processing step
d) Deliming and tanning for removing epidermis and skin residues and for lowering the pH value
e) Pickling for acidifying the pelts
f) Chroming, i.e., mineral tannage with chromium, aluminum or zirconium salts These processing steps are generally followed by a neutralization stage, possibly retannage, dyeing and greasing, and drying and dressing the leather to create ready-to-sell products. The processes mentioned above, except for drying and dressing, are carried out in the so-called limeyard. The containers used consist of paddles, drums, and machines that work according to the concrete mixer or washing machine principle. Enzymes are used in the above-mentioned processing steps up to and including the pickling stage. It is obvious that leather-chemical processes and other applications of proteolytic enzymes in the pH range from 3 to 12 require different types of enzymes to be used in the individual processing steps since each enzyme has a pH-dependent activity range. The range of an enzyme product for the manufacture of leather can be considerably expanded by making the enzymes with different pH activity ranges available in mixtures for use in the manufacture of leather goods. The protease mutants according to this invention can be used to special advantage in the leather manufacturing industry mainly in the processing step that involves hair removal (in the beamhouse). The mutants according to this invention are characterized by the fact that they ensure optimum efficacy with respect to the dissolution of the proteins responsible for hair fixation up to a pH value of pH 12, especially at the low temperatures (approximately 28° C. to 30° C.) prevailing during the industrial hair removal step. The useful hair removal effect is additionally supported by an increased pH stability of the protease triple mutant according to this invention. Using the protease triple mutant according to this invention, the hair can be very easily removed from the skins and hides, and it is possible to remove a very high percentage of the hair (more than approximately 99%). As demonstrated in the examples of a laboratory model test, the removal of the hair with a scraper is very easy. Thus, the protease triple mutants according to this invention make it possible to enzymatically remove the hair even from skins and hides of large animals completely and with damage in a manner that meets the practical requirements. Furthermore, using the protease triple mutant according to this invention, the use of environmentally detrimental chemicals (such as sulfide) in the beamhouse can be largely avoided.

Another subject matter of this invention quite generally concerns compositions for industrial applications which contain the above-described high-alkaline protease according to this invention as well as other ingredients conventionally used in such formulations for a specific targeted application. For example, for applications such as the industrial cleaning of hard surfaces, the compositions according to this invention contain the following typical ingredients: alkalis (e.g., NaOH, KOH), anionic and nonionic surfactants, complexing agents, peroxygen bleaching agents, propylene glycol and organic solvents, phosphonates and builders. For the leather manufacturing industry, typical compositions according to this invention frequently contain sodium sulfate, ammonium sulfate, sawdust and other ingredients as formulation components. These compositions are available as solid products which consist of mixtures of powdered constituents and granules.

In addition to the above-described advantages of the high-alkaline bacillus protease mutants according to this invention in industrial applications, the protease mutants according to this invention also have surprising advantages when used in household detergent and householder cleaner compositions which contain the high-alkaline protease mutant according to this invention in combination with another conventionally used prior-art protease of the "subtilisin 309"-type (which does not contain the triple mutation N42R/N114R/N115R). The high-alkaline protease mutant according to this invention, in a mixture with a protease that is normally used for this particular domestic application, has a positive effect on the residual washing power after storage of the household detergents. By adding the high-alkaline protease according to this invention, the storage stability of the conventional household detergent and household cleaner proteases is considerably increased in the presence of the conventionally used ingredients in the detergents and cleaning agents. In contrast to the compositions which contain the conventionally used prior-art proteases and which experience not only an observable loss of activity but also a decrease of the washing power, the use of the protease triple mutant N42R/N114R/N115R ensures that, with respect to the conditions of universal household detergents (pH=9.5 to 10.5, washing temperatures especially of 30° C. to 60° C.), an optimum detergent effect is maintained during the storage and delivery periods that are normal in the distribution of these compositions, which effect by far exceeds the detergent effect of compositions that contain only the protease known from prior art.

This invention therefore also concerns household detergent and household cleaner compositions which contain a high-alkaline protease mutant according to this invention in combination with another protease of the "subtilisin 309"-type that does not contain the triple mutation N42R/N114R/N115R. Useful household detergent and household cleaner compositions according to this invention contain the high-alkaline protease mutant according to this invention in combination with another protease, the amino acid sequence of which has a 95%, preferably a 98%, homology with respect to the amino acid sequence shown in FIG. 1, with the other protease, however, not containing the triple mutation N42R/N114R/N115R. Especially preferred are household detergent and household cleaner compositions which contain a high-alkaline protease according to this invention, the underlying amino acid sequence of which is substantially identical to the amino acid sequence shown in FIG. 1. Preferred are those high-alkaline proteases according to this invention with the mutation N42R/N114R/N115R, the underlying amino acid sequence of which is identical to the amino acid sequence shown in FIG. 1 or differs only in position 85 due to the natural difference asparagine instead of serine.

The applications and compositions according to this invention should preferably use those alkaline bacillus protease preparations according to this invention that have an enzyme activity of 50,000 to 1,000,000 DU/g of enzyme preparation. "DU" is the enzymatic activity in Delft units, where 1,000 DU correspond to the proteolytic activity which, given a volume of 1 mL of a 2% w/w enyzme solution and after decomposition of the casein, results in an extinction difference (1 cm light path; 275 nm; determination against a blind test) of 4,000. The alkaline bacillus protease preparations according to this invention can be used in the formulations conventionally used for industrial processes either by themselves or, optionally, in combination with other proteases normally used in industrial or household applications or other substantially conventional enzymes, such as amylases, lipases, cellulases, pectinases, nucleases, oxido reductases, etc. Relative to the dry substance of the overall preparation, the bacillus proteases mentioned should preferably be present in the formulations according to this invention in quantities of 0.1 to 5 wt %, especially of 0.2 to 2 wt %.

The compositions according to this invention can be manufactured for the different fields of application according to substantially known methods in the form of a powder, e.g., in the form of granules, prills, or pellets, optionally covered with a surface coating. Due to the excellent stability of the bacillus protease mutants according to this invention, these can also be used in liquid formulations.

Under the conditions normally used in industrial processes—such as highly alkaline pH values, e.g., pH values above 11.0, and optionally high temperatures up to 70° C.—the high-alkaline bacillus protease mutant according to this invention has surprisingly good properties. This is especially surprising since, in contrast to normal household applications, the application times used in industrial applications are in most cases relatively short. In addition to a high temperature resistance, the high-alkaline bacillus protease mutant according to this invention has a high enzyme stability in the presence of conventional ingredients for industrial compositions as well as for household applications. The high-alkaline bacillus protease mutant according to this invention is also surprisingly resistant to the bleaching agents that are normally used in industrial compositions or in household applications, such as industrial disinfecting detergents for hospital applications as well as household detergents.

Explanations relating to the figures:

FIG. 1:

Sequence protocol of the amino acid sequence (SEQ ID NO1) of alkaline protease from *Bacillus alcalophilus* HA1 (DSM 5466).

FIG. 2:

Optimum pH value of the protease mutant in comparison with the nonmutated original protease at T=50° C.

FIG. 3:

Optimum temperature of the protease mutant in comparison with the nonmutated original protease at pH=11.

FIG. 4:

Storage stability of the protease mutant in comparison with the nonmutated starting protease in a standard detergent. The closed circles indicate the residual activity and the solid bars indicate the detergent power of the detergent containing the protease mutant. The open circles indicate the residual activity and the diagonally striped bars indicate the detergent power of the detergent containing the nonmutated starting protease.

FIG. 5:

Detergent power of the protease mutant in comparison with the nonmuted starting protease at pH=11.4 and T=15° C. to 60° C.

Sequencing the amino acid sequence (shown in FIG. 1) of the alkaline protease from *Bacillus alcalophilus* HA1 (DSM 5466) by way of determining the corresponding nucleotide sequence is described in Examples 1 through 4 of the European Patent Application EP 415,296. Strain HA1 of *Bacillus alcalophilus* was deposited on Jul. 28, 1989, with the Deutsche Sammlung von Mikroorganismen (DSM; German equivalent of ATCC) under number DSM 5466 (address: DSM—Deutsche Sammlung von Miroorganismen und Zellkulturen GmbH, Mascheroder Weg 1b, D-38124 Braunschweig, Federal Republic of Germany).

EXAMPLES

The following examples will explain this invention in greater detail without in any way limiting the scope of the invention.

Example 1

Preparation of the alkaline protease which was varied by mutation in the amino acid sequence The alkaline protease which differs from the amino acid sequence shown in FIG. 1 of the alkaline protease from *Bacillus alcalophilus* HA1 (DSM 5466) in the amino acid exchanges N42R, N114R, and N115R was prepared according to substantially known methods by directed mutagenesis in DNA subsegments of the corresponding protease gene. The numbers indicate the position in the amino acid sequence shown in FIG. 1, with the original amino acid preceding the numerical position in the substantially known one-letter code and the introduced amino acid following the numerical position. The process of directed mutagenesis for single mutations is described in detail in Examples 5 through 18 of the European Patent Application EP 415,296. Also, with respect to carrying out the process for producing single mutations, reference is made to the examples of the European Patent Application EP 503,346.

The process includes the following substantially known processing steps:

Following the method of Saito et al. (1963, Biochim. Biophys. Acta 72, pp. 619–629), chromosomal DNA was isolated from the natural isolate *Bacillus alcalophilus* HA1 (DSM 5466) and partially hydrolyzed with the restriction endonuclease Sau3A. The restriction fragments were fractionated by means of electrophoresis and the fragments were isolated in sizes of 3 to 8 kilobases. The isolated and size-selected DNA fragments from *Bacillus alcalophilus* HA1 were newly combined in vitro with vector DNA of the substantially known plasmid pUB 110 according to substantially known methods. Using the method described by S. Chang and N. Cohen (1979, Mol. Gen. Genet. 168, pp. 111–115), protoplasts of the strain *Bacillus subtilis* BD224 (Bacillus Genetic Stock Center 1A46) were transformed with the obtained DNA that was newly combined in vitro. The transformants were selected on plates with neomycin. According to the manual by Maniatis et al. (Maniatis et al.=T. Maniatis, E. F. Fritsch, J. Sambrook, Molecular Cloning, A Laboratory Manual, Cold Spring Harbor Laboratory, 1982), the plasmid DNA was isolated from a clone. The fragment from *B. alcalophilus* DNA that was contained in this plasmid had a size of 4.1 kilobases and contained the complete DNA sequence for the high-alkaline protease from *Bacillus alcalophilus* HA1 (DSM 5466) (see Examples 1 and 2 of the European Patent Application EP 415,296).

The plasmid which contained the complete DNA sequence for the high-alkaline protease from *Bacillus alcalophilus* HA1 (DSM 5466) was cut with AvaI. The protruding ends were filled according to substantially well-known methods (Maniatis et al., p. 114) to form a DNA double strand. After subsequently restricting this DNA with XbaI, the N-terminal fragment comprising 1.618 BP was isolated and cloned according to substantially known methods into the vector pBS. The resulting vector contained the N-terminal end for the DNA that codes for the amino acid sequence shown in FIG. 1 (see Example 5 of the European Patent Application 415,296).

Using a similar method, a vector was created which contained a DNA fragment which comprises 658 BP and which codes for the C-terminal end of the corresponding protease. For this purpose, the plasmid that contained the complete DNA sequence was cut with the restriction endonucleases XbaI and Asp718 and cloned into the cutting site of the known vector pBS (see Example 7 of the European Patent Application 415,296).

Using the "primer extension" technique described by T. A. Kunkel (1985, Proc. Natl. Acad. Sci. USA 82, pp. 488–492), the directed mutations were carried out in the DNA subsequence that contained the C-terminal or the N-terminal end. For this purpose, the corresponding vectors were first transformed according to substantially known methods into their uracilated single-strand analogs by cultivating transformed *E. coli* CJ236 bacteria which were additionally infected with the helper phage M13 K07 (obtained from Bio-Rad Laboratories, Richmond, Calif.), with one of the two vectors. The bacterium *E. coli* CJ236 is [word or words missing] to a substantially known defective uracil-N-glycosylase which during the replication of the vectors, incorporates the nucleotide uracil instead of thymidine into the DNA sequence of the vector. Uracilated vectors can be used to advantage according to substantially known methods for in-vitro reactions of the directed mutagenesis since the uracil-containing single DNA strand which served as a matrix to generate mutated DNA strands can be removed after conclusion of the reactions by treating it with uracil-N-glycosylase. The use of the helper phages mentioned was required for the synthesis of the envelope proteins for the uracilated single-strand vector DNA that formed. Uracilated single-strand envelope vector DNA was extracted from the transformed host organism *E. coli* CJ236 and subsequently isolated from the culture medium.

The isolated uracilated DNA single-strand vectors of the C-terminal or N-terminal end were hybridized with synthetic oligonucleotides which contained the mutation sites and, at the same time, served as primers for the subsequent completion of the complete DNA double strand with mutation. The synthetic oligonucleotides used were produced according to substantially known methods according to the process described by S. L. Beaucage and M. H. Caruthers (1981, Tetrahedron Letters 22, pp. 1859–1862). The synthesis of the second DNA strand was carried out according to substantially known methods by means of T4 DNA polymerase and subsequent ligation with T4 DNA ligase (Kunkel et al., 1987, Methods in Enzymol. 154, pp. 367–382). The double-strand vector DNA that formed was transformed in *E. coli* MC 1061 and the mutated vectors were identified by examining the corresponding unitary restriction endonuclease recognition sites which were introduced or removed with the synthetic oligonucleotides.

To produce, e.g., two mutations either in the N-terminal or in the C-terminal portion of the protease DNA, the process, after introducing a first mutation, was repeated by using a further synthetic oligonucleotide to introduce a second mutation.

Expression vectors with mutations in the C-terminal portion or the N-terminal portion of the protease DNA sequence were produced by cutting the DNA sequences, which were obtained by means of the directed mutagenesis, with restriction endonucleases and by ligating them with a vector DNA which contained the other terminal portion of the DNA sequence and all elements required for the expression. The vectors obtained were complete expression vectors with a suitable reading frame for the expression of the correspondingly mutated protease. Expressions vectors of this type were produced following the method that is explained in greater detail in Example 16 of the European Patent Application EP 415,296. For the subsequent triple mutation, the expression vector DSM 5466 Mut. N42R/N114R/115R was produced using the same process.

The triple-mutated high-alkaline protease was produced by transforming and cultivating *B. subtilis* BD 224 with the above-mentioned expression vector using a substantially known method. The triple-mutated high-alkaline protease was isolated from the protruding culture of the transformed and cultivated strain according to well-known methods. A detailed description of the method for isolating mutated proteases can be found in Examples 16 and 18 of the European Patent Application EP 415,296 on which this work was based.

The alkaline protease on the basis of *Bacillus alcalophilus* HA1 (DSM5466) which was varied as a result of the triple mutation in the amino acid sequence was used in the tests described in Examples 2 through 4.

The application and the advantages of the triple mutant according to this invention in industrial textile laundering processes are described in greater detail in the examples of the parallel and priority-establishing German Patent Application DE 4,411,223 to which reference is hereby made.

Other properties of the protease mutant according to this invention are listed in Example 5.

Example 2

Determination of the hair removal property of the protease triple mutant according to this invention Preliminary cleaning:

The cowhide is soaked in twice the quantity of water (relative to the cowhide) for 1 h with 0.1% of Marlipal 013/939 at approximately 28° C.–30° C. The cowhide is subsequently cut into pieces measuring approximately 20×60 cm and stored at −20° C. From these stored cowhide pieces, test samples measuring approximately 20×7 cm are cut, the excess water is allowed to drip off, and the samples are dried with paper towels. The test samples are [word or words missing; probably: incubated] for 120 min in a solution with 0.5% soda and 0.1% [word or words missing] stirred for 15 min. The increase in weight is recorded.

| A. Swelling (water absorption) of the precleaned hides | | | | | |
|---|---|---|---|---|---|
| Incubation solution: | | 0.5% Na carbonate, 0.1% Marlipal (relative to the hide), twice the quantity of water (relative to the hide) | | | |
| Incubation time: | | 120 min | | | |
| Incubation temperature: | | 28° C. | | | |
| Enzyme: | | Optimase L660 | | | |
| Enzyme Dosage | | Weight after | Weight before | Difference increase in | |
| (g/100 kg | | incubation | incubation | weight | |
| Test cowhide) | [AADU/kg] | [g] | [g] | [g] | [%] |
| 1     6,08 | 37470 | 729,53 | 701,59 | 27,940 | 4,0 |
| B. Hair removal | | | | | |
| Incubation solution: | | 7.1 g/L Ca(OH)2 (200% relative to the cowhide) | | | |
| Incubation time: | | 24 h | | | |
| Incubation temperature: | | 30° C. | | | |
| Mixing: | | At the beginning of the incubation, 2 h continuously in the Linitest machine and at the end, 3.5 hours continuously | | | |
| pH value: | | Beginning: 12.48 End: 12.45 | | | |
| Container No. | Protease | Enzyme Dosage | | Removal of the Skin | |
| 1 | Blind Test | — | — | 3 | |
| 2 | Blind Test | — | — | 3 | |
| 3 | Mutant | 310,81 | 925188 | 1 | |
| 4 | Mutant | 310,81 | 925188 | 1 | |

Mutant = protease triple mutant N42R/N114R/N115R with activity of 300.000 DU/mL (+5%)
1: Easy and complete removal of the hair
2: Almost complete removal of the hair but still some (lumpy) residues on the skin
3: Only very few hairs or no hairs at all are removed.

Commentary: After processing step A, the test samples were soft and spongy, after processing step B, the test samples had "hardened into a rubberlike texture."

Example 3

Origin of the test samples: cow, back

Preliminary cleaning:

The cowhide is soaked in twice the quantity of water (relative to the cowhide) for 1 h with 0.1% of Marlipal 013/939 at approximately 28° C.–30° C. The cowhide is subsequently cut into pieces measuring approximately 20×60 cm and stored at −20° C. From these stored cowhide pieces, test samples measuring approximately 20×7 cm are cut, the excess water is allowed to drip off, and the samples are dried with paper towels. The test samples are [word or words missing; probably: incubated] for 120 min in a solution with 0.5% soda and 0.1% [word or words missing] stirred for 15 min. The increase in weight is recorded.

Under the conditions listed below, 3 tests were carried out.

| A. swelling (water absorption) of the precleaned hides | |
|---|---|
| Incubation solution: | 0.5% Na carbonate, 0.1% Marlipal (relative to the hide), twice the quantity of water (relative to the hide) |
| Incubation time: | 120 min |
| Incubation temperature: | 28° C. |
| Enzyme: | Optimase L660 |

| | Enzyme Dosage | | Weight after incubation | Weight before incubation | Difference increase in weight | |
|---|---|---|---|---|---|---|
| Test | (g/100 kg cowhide) | [AADU/kg] | [g] | [g] | [g] | [%] |
| 1 | 15,89 | 20060 | 715,98 | 732,58 | −16,60 | −2,3 |
| 2 | 3,26 | 20122 | 905,27 | 866,22 | 39,05 | 4,5 |
| 3 | 3,32 | 20476 | 338,39 | 342,25 | −3,86 | −1,1 |

** Between step A and B, the test specimens were stored in the refrigerator for 1.5 h.

| B. Hair removal | |
|---|---|
| Incubation solution: | 7.1 g/L Ca(OH)$_2$ (200% relative to the cowhide) |
| Incubation time: | 24 h |
| Incubation temperature: | 30° C. |
| Mixing: | At the beginning of the incubation, 2 h continuously in the Linitest machine and at the end, 3.5 hours continuously |
| pH value: | Beginning: End: |
| | Test 1    12.48    12.46 |
| | Test 2    12.55    12.53 |
| | Test 3    12.5     12.5 |

Results of test 1:
Protease used: Mutant N42R/N114R/N115R with an activity of 300.000 DU/mL (±5%)

| Container | Enzyme Dosage | | Removal of |
|---|---|---|---|
| No. | (g/100 kg cowhide) | [AADU/kg cowhide] | the Skin* |
| 1 | — | — | 3 |
| 2 | — | — | 3 |
| 3 | 31,2 | 92745 | 1,4 |
| 4 | 31,2 | 92745 | 1,2 |

Commentary: A certain amount of the hair was uniformly removed but a stubble of approximately 1–3 mm remained.

Results of test 2
Protease used: Mutant N42R/N114R/N115R with an activity of 300.000 DU/mL (±5%)

| Container | Enzyme Dosage | | Removal of |
|---|---|---|---|
| No. | (g/100 kg cowhide) | [AADU/kg cowhide] | the Skin* |
| 1 | 10,1 | 29969 | 2,2 |
| 2 | 50,3 | 149844 | 1,8 |
| 3 | 100,7 | 299688 | 2,0** |
| 4 | 151,0 | 449531 | 1,4** |

** Neck portion with a stronger growth of hair

Results of test 3
Protease used: Mutant N42R/N114R/N115R with an activity of 300,000 DU/mL (±5%)

| Container | Enzyme Dosage | | Removal of |
|---|---|---|---|
| No. | (g/100 kg cowhide) | [AADU/kg cowhide] | the Skin* |
| 1 | 151,3 | 450294 | 1,2 |
| 2 | 100,9 | 300196 | 1,4 |
| 3 | 50,4 | 150098 | 1,6 |

Legend referring to Test 1 to 3
1: Easy and complete removal of the hair
2: Almost complete removal of the hair but still some (lumpy) residues on the skin
3: Only very few hairs or no hairs at all are removed.

Example 4

| A. Main soaking cycle | | |
|---|---|---|
| Cowhide (weight): | 1886.25 g (precleaning same as in Example 2 and 3) | |
| Body part: | Belly | |
| Formulation: | Water: | 3772.50 g |
| | Na$_2$CO$_3$: | 3.43 g |
| | Surfactant: | 1.89 g Marlipal |
| | Enzyme: | 0.4046 g optimase L660 |
| | corresponds to: | 99582 AADU/kg cowhide |
| Weight after a reaction for 4 h: | | 2039.5 g |
| Increase in weight: | | 8.1 wt % |
| pH value after 0 reaction for 4 h: | | 10.21 |

| B. Hair removal | |
|---|---|
| Water: | 3059.25 g |
| Ca(OH)2 | 20.40 g |
| Enzyme: | 6.9352 g protease mutant with an activity of 150,000 DU/mL (±5%) |
| corresponds to: | 539878 AADU/kg cowhide | pH value after an incubation over 17.25 h: 12.75

Visual inspection of the hair removal results:

It was very easy to remove the hair; when the test sample was removed from the drum, the hair fell out as soon as the opening edge was touched. Only 2–3 areas measuring approximately 2 cm$^2$ remained but it was easy to remove the hair with a scraper.

Example 5

Figure 2:
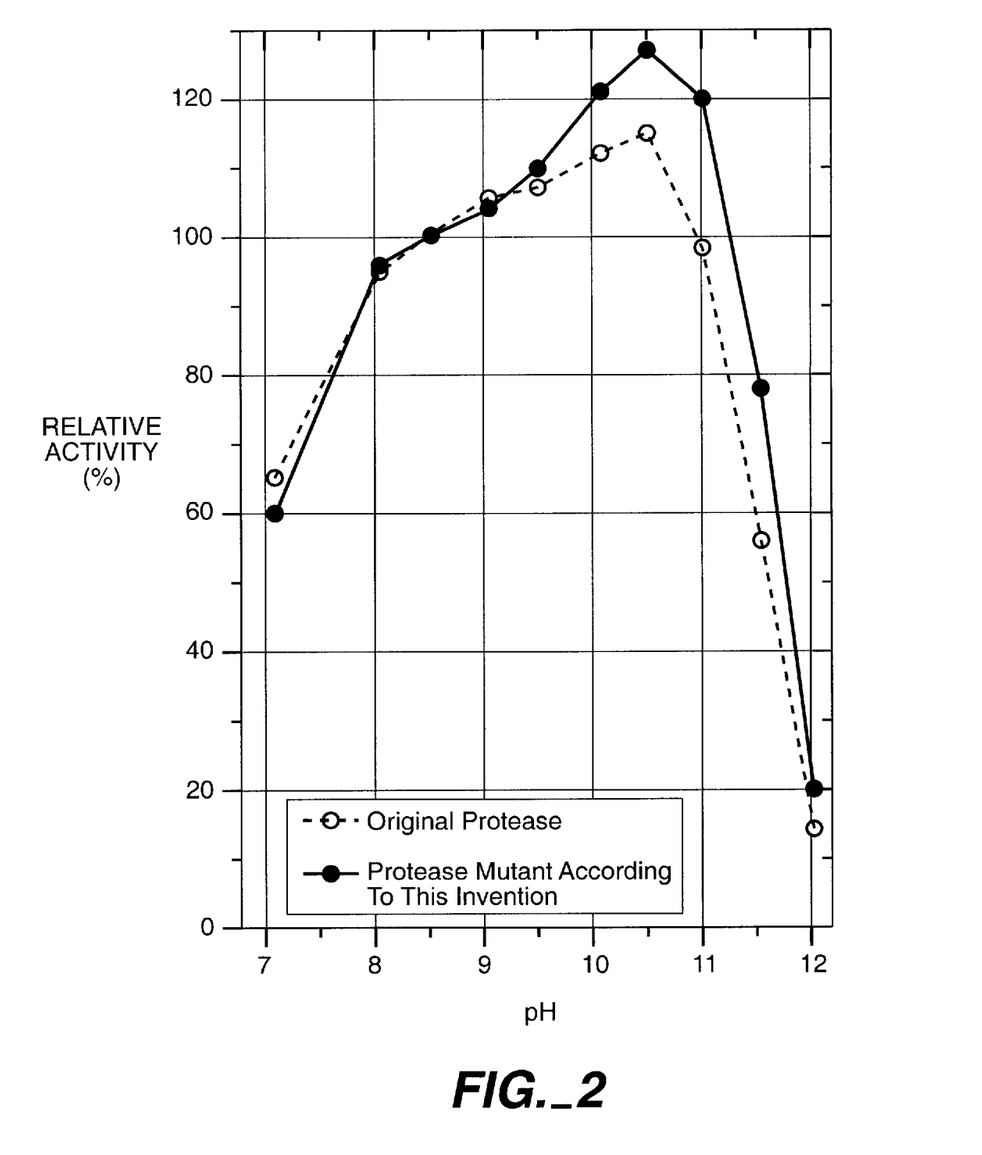
Figure 3:
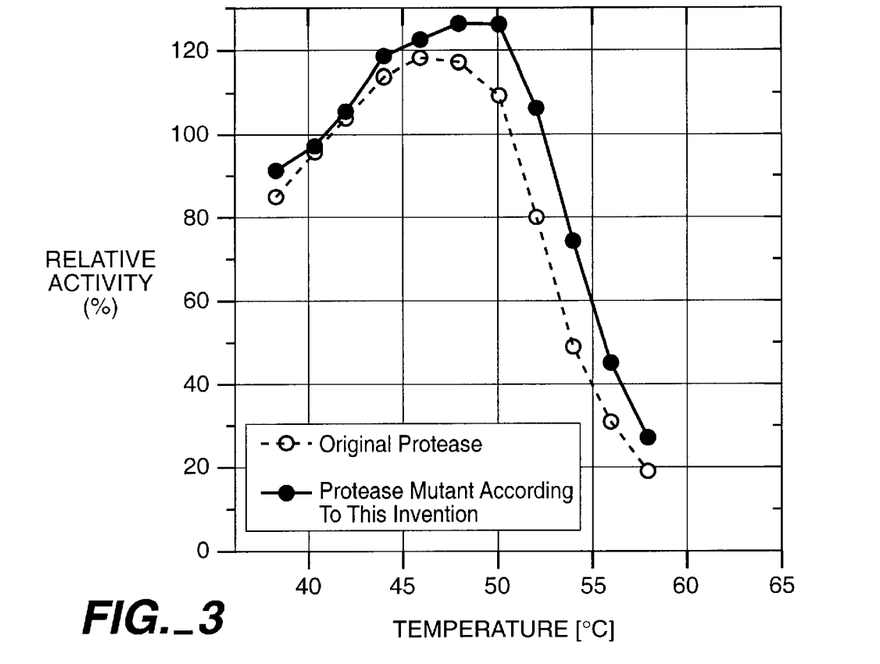
Figure 4:
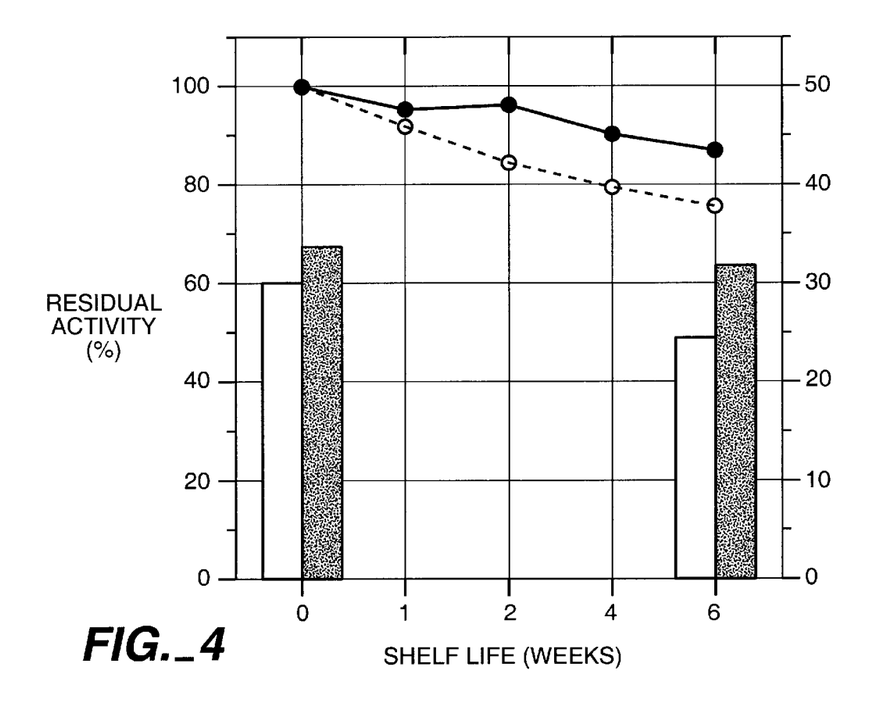
Figure 5:
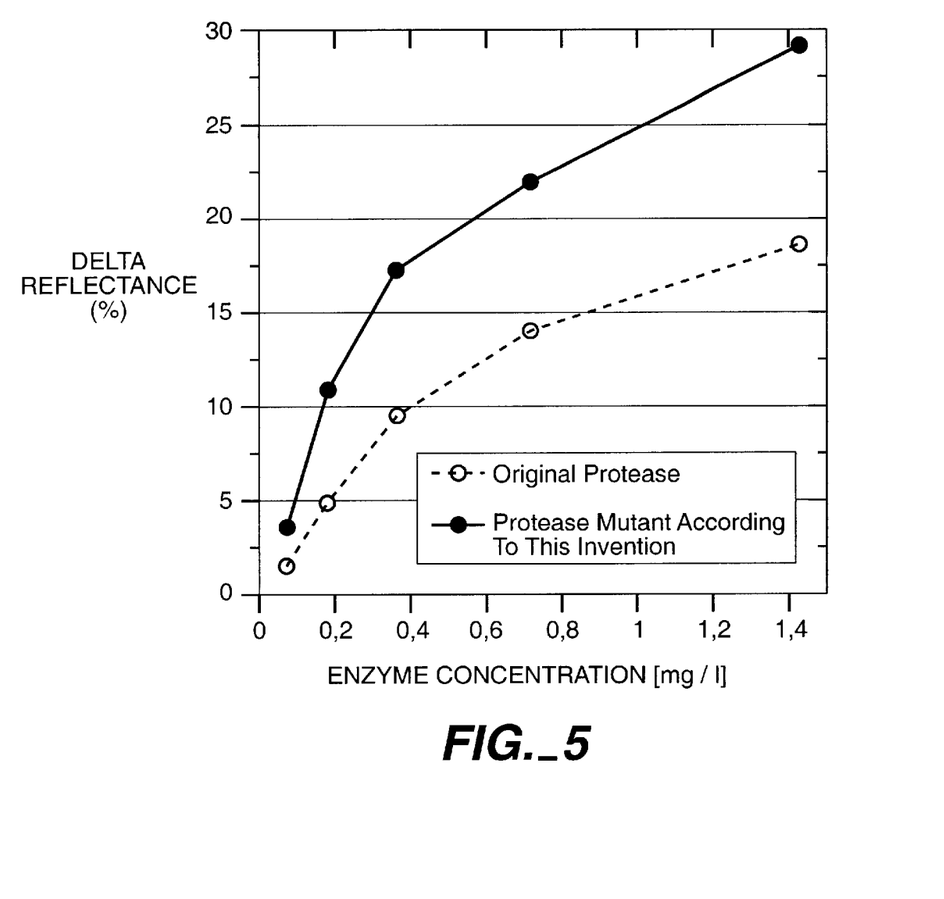

Below, a few other important properties of the triple mutant according to this invention will be explained.

a) The activity of the triple mutant was determined in comparison to the nonmutated original protease as a function of the pH value; the following conditions prevailed: substrate=acetyl casein, T=50° C., reaction time=10 min, phosphate borate buffer. The pH-dependent relative activity in % (the activity at pH=8.5 is defined as 100%) is shown in FIG. 2. At higher pH values in a range from pH=10 to 12, the triple mutant according to this invention is considerably more active than the original protease.

b) The activity of the triple mutant according to this invention in comparison to the nonmutated original protease as a function of the temperature was determined under following conditions: substrate=acetyl casein, pH=11. The temperature-dependent relative activity in % (the activity at pH=8.5 and T=50° C. is defined as 100%) is shown in FIG. 3. At the high pH value chosen and in the temperature range from 45° C. to 58° C., the triple mutant according to this invention is considerably more active than the original protease.

c) The shelf life of the triple mutant according to this invention in comparison with the nonmutated original protease as a function of the shelf life was determined by storing the triple mutant in a standard heavy-duty detergent under the following conditions: T=30° C., 60% relative humidity (r.h.), in closed boxes. The residual activity in % determined after storage (relative to the original activity=100%) of the triple mutant according to this invention is considerably higher, thus also improving the stability. The results are shown in FIG. 4.

d) To demonstrate the high-quality cleaning effect (cleaning hard surfaces) of the triple mutant according to this invention, the detergent power was compared to that of the original protease and determined for different enzyme concentration under the following conditions: standard detergent base; pH=11.4 (6 g/L); test fabric=EMPA 117, T=60° C. The results found (delta reflectance) as a function of the enzyme quantity used (mg/L) are illustrated in FIG. 5, which shows the superiority of the protease according to this invention at high pH values and an increased temperature.

e) To demonstrate the advantages of the combination of the triple mutant according to this invention with the prior-art detergent proteases (in this case, the original protease of the "subtilisin 309"-type), the following tests were carried out which led to the results indicated.

Test 1

Relative detergent power of the triple mutant according to this invention in comparison with the nonmutated original protease (covered with a coating) prior to and after storage in a heavy-duty detergent for household applications. This detergent power is the average detergent power obtained from 2 test fabrics with doses of the same activity.

| Protease | Prior to storage | After 6 weeks of storage at 35° C./80% r.h. |
|---|---|---|
| Original protease | 97,15 | 28,15 |
| Triple mutant | 66,22 | 50,72 |
| N42R/N114R/N115R | 61,60 | 50,79 |

Test 2

Residual activity and residual detergent power after storage of the triple mutant according to this invention an the original protease in detergent powder at 30° C. and 60% r.h. (relative humidity); pH value prior to washing is 10.2.

| Storage time | A | B | C | D |
|---|---|---|---|---|
| 0 Weeks | 100,0 | 24,50 | 100,0 | 22,99 |
| 1 Week | 92,4 | — | 100,0 | — |
| 2 Weeks | 86,9 | — | 94,6 | — |
| 4 Weeks | 75,1 | — | 86,0 | — |
| 6 Weeks | 60,9 | 14,98 | 70,8 | 21,63 |

Test fabric: Blood/milk/ink (EMPA 117)

% dR: Difference between the reflection of the test fabric (enzyme-containing detergent) and the reflection of the test fabric that was washed with enzyme-free detergent base.

Enzyme dose: Same activity

A=Residual activity (%), original protease

B=Detergent power (% dR), original protease

C=Residual activity (%), triple mutant

D=Detergent power (% dR), triple mutant

Definitions

Optimase L660=alkaline protease from *B. licheniformis*

Marlipal=polyethylene glycol isotridecyl ether

Walocel=2-hydroxyethyl cellulose ether

Sequinon=[[bis[2-[bis(phosphonomethyl)amino]ethyl]amino]-methyl] phosphonic acid, sodium salt Rewoteric=ampholyte on the basis of imidazoline EMPA117=test fabric of polyester/cotton with contamination of blood/milk/ink (Swiss Materials Testing Institute)

What is claimed is:

1. An industrial process comprising cleaning a hard surface using a modified subtilisin protease wherein a substitution of arginine for the amino acids occurs at each of the amino acid positions homologous to positions 42, 114 and 115 of SEQ ID NO: 1.

2. The process of claim 1, wherein said hard surface is in an industrial plant.

3. The process of claim 1, wherein said hard surface is in a location in the food industry.

4. The process of claim 3, wherein said location selected from the group consisting of slaughtering plants, institutional kitchens, and grill restaurants.

5. A cleaning process comprising the application of a modified subtilisin protease to the manufacture of leather, wherein said modified subtilisin protease comprises a substitution of arginine for the amino acids occurring at each of the amino acid positions homologous to positions 42, 114 and 115 of SEQ ID NO: 1.

6. The process of claim 5, wherein said application of said modified subtilisin protease is used for removing hair from skin or hide.

7. A composition for industrial applications comprising a modified subtilisin protease and at least one other ingredient conventionally used in formulations for cleaning hard surfaces, wherein said modified subtilisin protease comprises a substitution of arginine for the amino acids occurring at each of the amino acid positions homologous to positions 42, 114 and 115 of SEQ ID NO: 1.

8. The composition of claim 7, wherein said at least one other ingredient comprises an ingredient selected from the group consisting of a component which dissolves dirt, a compound for the removal of fatty acids, a corrosion-protection agent and an antifroth agent.

9. The composition of claim 8, wherein said component which dissolves dirt is selected from the group consisting of sodium hydroxide, potassium hydroxide, sodium carbonate, potassium carbonate, an alkaline salt of orthophosphoric acid, and soda and potash glass.

10. The composition of claim 8, wherein said compound for the removal of fatty acids is an alkyl phenol glycol ether.

11. A composition for use in the manufacture of leather comprising a modified subtilisin protease and at least one other ingredient conventionally used in formulations for manufacturing leather, wherein said modified subtilisin protease comprises a substitution of arginine for the amino acids occurring at each of the amino acid positions homologous to positions 42, 114 and 115 of SEQ ID NO: 1.

12. The composition of claim 11, wherein said at least one other ingredient comprises an ingredient selected from the group consisting of sodium sulfate, ammonium sulfate, calcium hydroxide, sodium carbonate, soda, a surfactant, and sawdust.

* * * * *

UNITED STATES PATENT AND TRADEMARK OFFICE
CERTIFICATE OF CORRECTION

PATENT NO. : 6,190,904 B1
DATED : February 20, 2001
INVENTOR(S) : Amory et al.

It is certified that error appears in the above-identified patent and that said Letters Patent is hereby corrected as shown below:

Title page,
Item [73], Assignee, delete "Genecor International, Inc." and insert -- Genencor International, Inc."

Signed and Sealed this

Eighteenth Day of December, 2001

Attest:

JAMES E. ROGAN
*Director of the United States Patent and Trademark Office*

*Attesting Officer*

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 380 amino acids
        (B) TYPE: amino acid
        (C) STRANDEDNESS: single
        (D) TOPOLOGY: linear (xi) SEQUENCE DESCRIPTION: SEQ ID NO:1:

```
Met Lys Lys Pro Leu Gly Lys Ile Val Ala Ser Thr Ala Leu Leu Ile
-110                -105                -100

Ser Val Ala Phe Ser Ser Ile Ala Ser Ala Ala Glu Glu Ala Lys
-95                 -90                 -85                 -80

Glu Lys Tyr Leu Ile Gly Phe Asn Glu Gln Glu Ala Val Ser Glu Phe
                -75                 -70                 -65

Val Glu Gln Val Glu Ala Asn Asp Glu Val Ala Ile Leu Ser Glu Glu
                -60                 -55                 -50

Glu Glu Val Glu Ile Glu Leu Leu His Glu Phe Glu Thr Ile Pro Val
            -45                 -40                 -35

Leu Ser Val Glu Leu Ser Pro Glu Asp Val Asp Ala Leu Glu Leu Asp
    -30                 -25                 -20

Pro Ala Ile Ser Tyr Ile Glu Glu Asp Ala Glu Val Thr Thr Met Ala
-15                 -10                 -5                   1

Gln Ser Val Pro Trp Gly Ile Ser Arg Val Gln Ala Pro Ala Ala His
                5                   10                  15

Asn Arg Gly Leu Thr Gly Ser Gly Val Lys Val Ala Val Leu Asp Thr
                20                  25                  30

Gly Ile Ser Thr His Pro Asp Leu Asn Ile Arg Gly Gly Ala Ser Phe
            35                  40                  45

Val Pro Gly Glu Pro Ser Thr Gln Asp Gly Asn Gly His Gly Thr His
50                  55                  60                  65

Val Ala Gly Thr Ile Ala Ala Leu Asn Asn Ser Ile Gly Val Leu Gly
                70                  75                  80

Val Ala Pro Ser Ala Glu Leu Tyr Ala Val Lys Val Leu Gly Ala Ser
                85                  90                  95

Gly Ser Gly Ser Val Ser Ser Ile Ala Gln Gly Leu Glu Trp Ala Gly
            100                 105                 110

Asn Asn Gly Met His Val Ala Asn Leu Ser Leu Gly Ser Pro Ser Pro
    115                 120                 125

Ser Ala Thr Leu Glu Gln Ala Val Asn Ser Ala Thr Ser Arg Gly Val
130                 135                 140                 145

Leu Val Val Ala Ala Ser Gly Asn Ser Gly Ala Gly Ser Ile Ser Tyr
                150                 155                 160

Pro Ala Arg Tyr Ala Asn Ala Met Ala Val Gly Ala Thr Asp Gln Asn
            165                 170                 175

Asn Asn Arg Ala Ser Phe Ser Gln Tyr Gly Ala Gly Leu Asp Ile Val
            180                 185                 190

Ala Pro Gly Val Asn Val Gln Ser Thr Tyr Pro Gly Ser Thr Tyr Ala
    195                 200                 205

Ser Leu Asn Gly Thr Ser Met Ala Thr Pro His Val Ala Gly Ala Ala
```

-continued

```
210                 215                 220                 225

Ala Leu Val Lys Gln Lys Asn Pro Ser Trp Ser Asn Val Gln Ile Arg
                230                 235                 240

Asn His Leu Lys Asn Thr Ala Thr Ser Leu Gly Ser Thr Asn Leu Tyr
                245                 250                 255

Gly Ser Gly Leu Val Asn Ala Glu Ala Ala Thr Arg
                260                 265
```